United States Patent [19]
Gaumer et al.

[11] Patent Number: 5,891,922
[45] Date of Patent: Apr. 6, 1999

[54] CLEANING AND DISINFECTANT BIOCIDE COMPOSITION, AND METHOD FOR CLEANING ANIMAL HUSBANDRY SURFACES

[75] Inventors: Gary E. Gaumer, Turlock, Calif.; Bruce A. Spielholz, Alpharetta, Ga.

[73] Assignee: Preserve International, Preserve, Inc., Turlock, Calif.

[21] Appl. No.: 915,056

[22] Filed: Aug. 20, 1997

[51] Int. Cl.⁶ .......... A01N 33/12; A01N 35/00; A01N 9/00; A61L 2/08
[52] U.S. Cl. .......... 514/643; 514/642; 514/705
[58] Field of Search .......... 514/642, 643, 514/705; 422/36, 27

[56] References Cited

U.S. PATENT DOCUMENTS

| | | | |
|---|---|---|---|
| 3,208,936 | 9/1965 | Hamilton | 252/1 |
| 3,282,775 | 11/1966 | Stonehill | 167/22 |
| 4,107,312 | 8/1978 | Wegner et al. | 424/263 |
| 4,455,287 | 6/1984 | Primack et al. | |
| 5,338,748 | 8/1994 | Wachman et al. | 514/358 |
| 5,344,838 | 9/1994 | Wachman | 514/358 |

FOREIGN PATENT DOCUMENTS

| | | | |
|---|---|---|---|
| 2625964 | 1/1977 | Germany. | |
| WO 9317558 A | 9/1993 | WIPO. | |

OTHER PUBLICATIONS

Union Carbide—Product Listings.

BASF—Product Listings.

Gelinas et al. Neutralization of the activity of eight disinfectants by organic matter, J. Appl. Bacteriol., 1983, 54, 243–7.

Gelinas et al. Effect of low concentration of eight disinfectants on a cheddar cheese starter, Lait 1982, 62, 660–70.

*Primary Examiner*—Jose' G. Dees
*Assistant Examiner*—Alton Pryor
*Attorney, Agent, or Firm*—Willie Krawitz

[57] ABSTRACT

A phase-stable, biocide concentrate and/or solution composition is provided for disinfecting surfaces such as in animal husbandry applications, food processing, medical purposes, and the like. In the concentrate form, the composition comprises a quaternary ammonium biocide, an aliphatic dialdehyde and a foam surfactant. Typically, the solution composition may employ glutaraldehyde, a foam producing surfactant, a chelating agent, an odor obscuring compound, and an acid to lower the pH and stabilize the glutaraldehyde. The concentrate has a stability at ambient temperature of up to about two years. When applied to surfaces employed in animal husbandry, the adhesive properties of the composition enable it to remain in contact with these surfaces a sufficiently long time and thereby provide effective cleaning and disinfecting capability.

9 Claims, No Drawings

CLEANING AND DISINFECTANT BIOCIDE COMPOSITION, AND METHOD FOR CLEANING ANIMAL HUSBANDRY SURFACES

BACKGROUND OF THE INVENTION

This invention relates to a new and improved composition for cleaning and disinfecting surfaces, such as for animal husbandry, and for food processing and handling.

The requirements for cleaning and disinfecting compositions of these types are numerous, and involve good adhesion to a surface, not only for animal husbandry applications, where lengthy contact times improve cleaning and disinfectant results, but also for uses in areas such as food and food handling.

Also, it is desired to improve the phase stability and storage life capability, and to reduce obnoxious odors frequently associated with these compositions. Further, it is desired to provide biodegradable compositions, where feasible, and to ensure they are reasonably safe for general consumer use.

Moreover, it would be desirable to provide a cleaning and disinfecting composition which is effective in hard water, for example up to about 2,000 ppm and, at a high challenge of organic material, up to about 20%. Additionally, it would be desirable to provide a composition operable over a wide pH range of for example 0–9, since this would produce suitable cleaning and disinfecting activity for numerous microorganisms.

Typical publications concerning these compositions include: U.S. Pat. Nos. 4,469,614; 4,654,374; 4,923,899; 4,983,635; 5,124,359; 5,252,606; 5,284,875; 5,322,856; 5,338,748; 5,344,838; and, French Patent 2,622,397. In addition to these patents, a brochure entitled, Cetylicide$^{R™}$ published by Cetylite Industries, Inc., discloses germicidal compositions for use with medical equipment. Some problems concerning the compositions described in these publications is that they do not provide long term storage life, have a limited pH range capability, and do not appear effective at high levels of water hardness.

French Patent 2,622,397 describes ethoxylated fatty alcohol surfactants, but their corresponding commercial product TH4+™ contains a foam depressor which acts within about 5–10 minutes to reduce foam. Moreover, the only described use of the French patent is for corrosion prevention of metallic supports.

U.S. Pat. Nos. 5,338,748 and 5,344,838 also describe use of compositions where corrosion is a problem, but they omit a surfactant. Also, these two patents suggest employing deadly arsenic and cyanide salts, and other salts such as lead, chromium and selenium with less deadly, but nevertheless possessing dangerous properties at relatively high concentration levels. Consequently, U.S. Pat. Nos. 5,338,748 and 5,344,838 do not appear suitable or intended for animal husbandry use including poultry ranching and/or egg processing, or associated with domestic farm animals, or exposure to humans.

By contrast, the present invention involves the food industry, especially for animal husbandry, for poultry facilities and transportation, and for egg processing including egg storage, candling, and handling.

THE INVENTION

According to the invention, there is provided a composition and method for cleaning and disinfecting surfaces such as animal husbandry surfaces, food processing and handling equipment.

Broadly speaking, the composition and method of this invention comprise a phase stable, biodegradable, biocidal quaternary ammonium halide, an aliphatic dialdehyde, and a foam surfactant. When employed to treat surfaces associated with animal husbandry such as in poultry farming, the foam properties of the surfactant enables the composition to closely adhere to the treated surface, rather than simply run off.

These foam properties permit the composition to react with microorganisms on the treated surface for a long time, and results in a more efficient disinfectant and cleaning operation. Also, the composition has a stability period of up to about two (2) years, compared with U.S. Pat. Nos. 5,344,838 and 5,338,748.

DESCRIPTION OF THE PREFERRED EMBODIMENTS

Preferred components of the present composition included: quaternary ammonium halide biocides such as alkyl ($C_{10}$–$C_{18}$) benzyl dimethyl ammonium chloride; an ethoxylated alkyl phenol surfactant, such as nonyl phenols; and, suitable aliphatic dialdehydes include 2–6 aliphatic dialdehydes such as glutaraldehyde, which is one of the preferred constituents.

Typical quaternary ammonium halide biocides are listed in U.S. Pat. No. 5,338,748 and they are incorporated herein by reference. However, while that patent employs alkanols and/or glycols to improve the solubility of the various components, alcohols such as alkanols, isopropyl alcohol and/or glycols are omitted from the composition of the present invention since they reduce or nullify the foaming capability of surfactants.

Typical ethoxylated alkyl phenol surfactants are described in McCUTCHEON'S, EMULSIFIERS & DETERGENTS, VOLUME 1, North American Edition, 1994, and incorporated herein by reference. While these types of surfactants tend to be nonionic, other foaming (and hence adhesive or sticky) types of surfactants could be useful. Preferred surfactants are $C_8$–$C_{18}$ alkyl phenols having an HLB range of about 13–15, and include the IGEPAL series CO-630 to CO-730; a suitable specific surfactant is IGEPAL CO-720 which is described as a nonionic, ethoxylated (12), $C_{12}$ nonyl phenol. When aerosol formulations are employed, foaming requirements can be reduced, and the HLB range can be lowered to about 12–15.

The use of ethoxylated alkyl phenol surfactants is surprising since, although a wide variety of applications for ethoxylated alkyl phenol surfactants are set forth in McCutcheon's, supra, none are known as having the adhesive properties suitable for animal husbandry purposes and in the presence of high ppm hard water, and with long term storage properties, and this includes the IGEPAL surfactant series.

Disinfectant compositions with similar components tend to have a highly unpleasant odor, and hence various ingredients may be incorporated into the composition of this invention for odor obscuring purposes. A mixture of pine oil and terpineol may used as the odor obscuring material, and they also possesses biocide properties. Additionally, the mixture of pine oil and terpineol provides an oil vehicle for the performance and enhancement of thermalfogging, and functions to impart residual activity. Other odor obscuring compounds may be employed such as citric acid, which has the added benefit of providing for pH adjustment.

A chelating agent may be used in the present composition to aid in the solubility of components, to counteract the effect of hard water, and to breakdown the coatings of spores. When used, the preferred chelating agent is E.D.T.A., and partial esters or salts of EDTA may also be used; an example of a salt of EDTA is tetrasodium ethylenediamine tetraacetate. Additionally, these and other useful chelating agents are noted in U.S. Pat. Nos. 5,338,748 and 5,344,838 and, these chelating agents are incorporated herewith. These chelating agents may be found in the following acids, full salts or partial salts of: oxalic acid, malonic acid, oxaldihydrixamic acid, diaminoglyoxime, dithiomalonic acid, glyoxime, maleic acid, fumaric acid, oxalacetic acid, diglycolic acid, oxalenediuramidoxime, tartaric acid, thiodiglycolic acid, iminodiacetic acid, nitrilotriacetic acid, dimethylglyoxime, hydrazine N,N-diacetic acid, citraconic acid, 2,4-pentanedione, N-methyliminodiacetic acid, glutaric acid, glutamic acid, aconitric acid (trans), gluconic acid, 1,2-cyclohexanediamine-N,N,N', N'-tetraacetic acid, itaconic acid, N'-benzylethylenediamine-N,N,N'-triacetic acid, diethylenetriamine-N,N,N'N'N"N"-pentaacetic acid, 2,2"-ethylenedioxybis(ethyliminodiacetic acid), 2,2'-oxybis (propyliminodiacetic acid), hexamethyldiamine-N,N,N' N'-tetraacetic acid, triethylenetetraminehexaactic acid, ethyl acetoacetate; and, 1,3,5-triaminocyclohexanehexaacetic acid.

The present composition has a pH range of about 0–9, and pH adjustment is obtained by adding a suitable acid, such as citric, phosphoric and/or sulfuric. Acetic acid is noted in U.S. Pat. No. 5,284,875 as tending to eliminate stickiness, and hence does not appear recommended for use with foam surfactants to provide pH adjustment.

Typical component concentration ranges of the present composition are, as follows: quaternary ammonium halide: about 20%–80%; dialdehyde: about 1%–15%; foam surfactant: about 2%–15%; chelating agent: up to about 9%; odor obscuring compound: up to about 7.5%; phosphoric acid, and the like: sufficient to lower the pH and stabilize the dialdehyde; and, water: balance.

A suitable concentrate of this invention is, as follows: alkyl ($C_{12}$–$C_{18}$) benzyl dimethyl ammonium chloride (50%): about 26.00%; glutaraldehyde (50%): about 7.00%; ethoxylated (12) nonyl phenol (surfactant): about 7.50%; E.D.T.A. (chelating agent): about 3.12%; pine oil: about 1.5%; terpineol: about 3.00%; and phosphoric acid (75%): about 1.155%; and, water: 50.725%, all parts by weight. The pH of this solution is sufficiently low to stabilize the glutaraldehyde and maintain its long term stability at ambient temperatures.

When applied to walls, ceilings and floors of animal husbandry surfaces as poultry hatcheries, poultry growing facilities, egg processing facilities, etc., the foam nature of the composition of this invention provides a contact time for about 5 minutes to about one (1) hour. These results can be attained at dilution levels of about 1:250 parts of water.

Tests of the composition, supra, were carried out at a dilution of 1:256, in the presence of 1,000 ppm water hardness at 5% serum as organic load, conforming with A.O.A.C. 15th edition, U.S. Environmental Pesticide assessment guidelines on environmental surfaces. It was found that this composition is effective as a bactericide, virucide, fungicide, mildewicide, and as a deodorant.

Hatchery facilities which may be cleaned and disinfected by the composition of this invention, include: hatchers and setters, poultry go-round, tray washing machines, central and portable fogging systems, evaporative coolers, humidifying systems, live haul equipment, including poultry busses and transfer trucks, vehicle wheels, boots and shoes, trays, coops, poultry boxes such as polyethylene, foot baths, feed bins, poultry breeder such as for chicken and turkey breeder, layer and grow-out houses.

A wide variety of surfaces may be cleaned and disinfected by the composition of this invention, and include: ceramic and glazed tile surfaces, stainless steel, aluminum, chrome, tin, zinc, galvanized metal, brass, glass, treated and untreated wood, polyethylene, polypropylene, PVC, vinyl, fiberglass, and polymers of nitrile, acrylic and urethane. For thermalfogging purposes, one quart of solution diluted to about 1:250 and dispersed in 10 micron particle sizes will saturate about 1,000 cubic feet of space. All person, poultry, livestock and pets must be vacated from a building or enclosure prior to thermalfogging, and all vents, doors, louvers, etc., should be closed.

The building should remain closed for a minimum of twenty-four (24) hours for treatment to occur, after which it can be aired and a minimum of twenty-four (24) to forty-eight (48) hours should elapse prior to repopulating with poultry or livestock. Persons should not enter a treated room for a minimum of twenty-four (24) to forty-eight (48) hours following treatment, and if less time is required for reentry, NIOSH/MSHA guidelines for respirator use should be followed, and proper clothes, etc. should be worn. Also, if items such as feeders and watering troughs were not removed or covered prior to thermalfogging, these items should be thoroughly washed and cleaned with detergent prior to reuse by poultry or livestock.

When spray treating the interior of poultry houses including items such as walls, ceilings, floors, stalls, fixtures, troughs, and areas traversed by poultry or animals, these should be washed down prior to application by the spraying treatment, and a contact time of about ten (10) minutes to about one (1) hour should elapse for treatment to take place. Prior to reuse, the walls, floors, ceilings and interior items should then be rinsed with potable water.

Typical bacteria which can be disinfected with the composition of this invention include: *staphylococcus aureus, staphylococcus pyogenes, streptococcus hemolyticus, streptococcus dysgalactiae, mycobacterium tuberculosis, salmonella typhosa, salmonella typhimurium, salmonella pulorum, hemophilus parasuis, clostridium perfringens, mycoplasma synoviae, mycoplasma hyopneumoniae, pasteurella multocida, klebsiella pneumoniae, staphylococcus epidermis, streptococcus agalactiae, streptococcus fecalis, listeria monocytogenis, mycobacterium tuberculosis, salmonella choleraesuis, salmonella enteritidis, pseudomonas aeruginosa, clostridium tetani, diplococcus pneumoniae, mycoplasma gallisepticum, escherichia coli, pasteurella hemolytica, alcaligenes faecalis, salmonella gallinarum, salmonella arizonae, salmonella schotimuelleri, staphylococcus hyicus, streptococcus pyogenes, haemophilus parasuis;* and, *bordetella bronchiseptica.*

Fungus types which may be disinfected by the composition of this invention include: *aspergillus fumigatus, aspergillus glacus, aspergillus nidulans, aspergillus flavus, aspergillus niger, fusarium solani;* and, *penicillium* variable.

Viruses which are disinfected by this composition include: myxoma virus, newcastle disease virus, infectious bursal disease virus (Gumboro), avian infectious bronchitis virus, avian infectious laryngotracheitis virus, avian reovirus, avian rotavirus, avian influenza virus, avian adenovirus, Marek's disease virus, herpes simplex, HIV (AIDS virus), pseudorabies virus, transmissible gastroenteritis virus, porcine rotavirus, parvo virus, avian leukosis virus; and, avipox virus.

The composition and method of this invention provide an effective biocide foam having a long term effect on treated animal husbandry surfaces, with a long shelf life, besides being biodegradable and safe for animals and humans when properly used.

We claim:

1. A phase stable, biodegradable concentrate of a cleaning, disinfectant and biocide composition for animal husbandry surfaces, and in the presence of hard water, consisting of:
   a.) a biocide quaternary ammonium compound: 20%–80%;
   b.) an aliphatic dialdehyde having from 2 to 6 carbon atoms: 1%–15%;
   c.) a surfactant for reducing surface tension, and for adhesion to the animal husbandry surface: up to 15%;
   d.) a chelating agent: up to 9%;
   e.) an odor obscuring compound: up to 7.5b;
   f.) one or more acids selected from the group consisting of citric, phosphoric and sulfuric sufficient to obtain a pH for stabilizing the dialdehyde in the concentrate; and,
   g.) water: 10%–75%, all parts by weight, the concentrate having a stability period of up to two years at ambient temperatures, a diluted solution of the concentrate being effective in hard water up to 1,000 ppm.

2. The concentrate of claim 1, in which the water dilution is about 1:250.

3. The concentrate of claim 1, in which the chelating agent is E.D.T.A.

4. The concentrate of claim 1, providing contact times of five minutes to at least one hour in animal husbandry operations, and having a stability period of up to at least two years at ambient temperatures.

5. The concentrate of claim 1, in which the odor obscuring solution comprises pine oil and terpineol, the terpineol also functioning as a bacteriostat and mildewicide, and imparting residual activity.

6. The concentrate of claim 1, in which the quaternary ammonium compound contains a benzyl group and an alkyl moiety, or having a long chain aliphatic and a lower alkyl moiety.

7. The concentrate of claim 1, consisting of: an odor obscuring solution of pine oil and terpineol; the chelating agent is E.D.T.A.; the surfactant is an ethoxylated, alkyl phenol, or phenoxy; and, the solution is effective in hard water up to about 1,000 ppm.

8. A phase stable, biodegradable, cleaning, disinfectant and biocide foam concentrate composition for animal husbandry surfaces, and in the presence of hard water, consisting of:
   a.) an alkyl ($C_{10}$–$C_{18}$) benzyl dimethyl ammonium chloride biocide: 5%–40%;
   b.) an aliphatic dialdehyde hating from 2–6 carbon atoms: 6%–30%;
   c.) a surfactant for producing foam activity, reducing surface tension, and for adhesion to the animal husbandry surface: up to 20;
   d.) a chelating agent: up to 9%;
   e.) an odor obscuring compound, up to 9%;
   f.) an acid sufficient to obtain a pH for stabilizing the aliphatic dialdehyde; and,
   g.) water: 10%–75%, all parts by weight, a solution of the concentrate having a pH sufficiently low to stabilize the dialdehyde, thereby imparting to the concentrate a stability period of up to at least two years at ambient temperatures, a dilute solution of the concentrate being effective in hard water up to 1,000 ppm.

9. The concentrate of claim 8, in which the surfactant is a $C_8$–$C_{18}$ alkyl phenol having an HLB of 12–15.

* * * * *